United States Patent [19]

Yates

[11] 4,383,120

[45] May 10, 1983

[54] THERMAL CATALYTIC HYDROSILYLATION OF CARBONYL COMPOUNDS

[75] Inventor: Ronald L. Yates, Midland, Mich.

[73] Assignee: The Dow Chemical Company, Midland, Mich.

[21] Appl. No.: 320,237

[22] Filed: Nov. 12, 1981

Related U.S. Application Data

[63] Continuation-in-part of Ser. No. 284,034, Jul. 17, 1981, Pat. No. 4,322,654.

[51] Int. Cl.³ .............................. C07F 7/08; C07F 7/18
[52] U.S. Cl. .................................................... 556/470
[58] Field of Search ......................................... 556/470

[56] References Cited

U.S. PATENT DOCUMENTS 3,450,737  6/1969  Colleuille ............................ 556/470
3,536,745  10/1970  Dear .................................... 556/470

FOREIGN PATENT DOCUMENTS 1060910  3/1967  United Kingdom ................ 556/470

*Primary Examiner*—Paul F. Shaver

[57] ABSTRACT

A process to form silyl ethers by contacting a carbonyl compound with an organosilicon hydride under reaction conditions in the presence of a catalyst, said catalyst being a heated transition metal carbonyl coordination compound.

11 Claims, No Drawings

THERMAL CATALYTIC HYDROSILYLATION OF CARBONYL COMPOUNDS

CROSS-REFERENCE TO RELATED APPLICATION

This application is a continuation-in-part of application Ser. No. 284,034, filed July 17, 1981, now U.S. Pat. No. 4,332,654, issued June 1, 1982.

BACKGROUND OF THE INVENTION

This invention relates to an improved catalytic process for preparing silyl ethers. In particular, the invention relates to a process for preparing silyl ethers by catalysis of carbonyl compounds with organosilicon hydrides in the presence of Group VIII elements.

It is known to produce silyl ethers by reacting carbonyl compounds with organosilicon hydrides in the presence of catalysts. Such a process which utilizes a phosphine halo-rhodium catalyst is disclosed in U.S. Pat. No. 3,856,843. There, suitable carbonyl compounds such as aldehydes and ketones are shown as well as suitable organosilicon hydrides. Preparation of vinyloxy-containing organosilicon compounds using zinc chloride as a catalyst is shown in U.S. Pat. No. 3,472,888. Reaction of acetone with silane at high temperatures (300° C.–600° C.) is described in U.S. Pat. No. 3,069,451. This patent also discloses that ultraviolet light may be used to catalyze the reaction.

SUMMARY OF THE INVENTION

The present invention is an improved process for making silyl ethers which process comprises contacting a carbonyl compound with an organosilicon hydride in the presence of a catalytic amount of a transition metal carbonyl coordination compound under conditions sufficient to produce a silyl ether.

DETAILED DESCRIPTION OF THE INVENTION

The invention employs as a reactant a carbonyl compound or mixtures thereof. Suitable carbonyl compounds include ketones, esters and aldehydes with or without side chains or substituents. A few common examples are aliphatic ketones or aldehydes, aromatic ketones or aldehydes, and terpene ketones or aldehydes. Preferred examples are acetone, 2-heptanone, cycloheptanone, n-butyraldehyde and acetophenone.

The invention also employs as a reactant an organosilicon hydride. Necessary is an organosilicon hydride having at least one active Si-H group. Therefore, e.g., disilicon compounds are encompassed by the invention. Suitable organosilicon hydrides include those of the formula $H_xSiR_y$ wherein R is hydrocarbyl such as alkyl, aryl, arylalkyl, alkylaryl, and either straight-chained, branch-chained or cyclo or combinations thereof; and $x=1$ or 2; $y=2$ or 3 and $x+y=4$. Examples of these suitable compounds include trialkylsilanes such as triethylsilane, diethylmethylsilane and tributylsilane; dialkylsilanes; diarylalkylsilanes; diarylsilanes; arylalkylsilanes; alkylarylsilanes and arylsilanes. Preferred alkyl groups are the lower alkyl groups having 1-7 carbon atoms. The preferred aryl group is phenyl. Examples of preferred organosilicon hydrides are triethylsilane, diethylsilane, dimethylphenylsilane and diethylmethylsilane.

Suitable compounds for the process of this invention which exhibit catalytic activity upon heating are Group VIII transition metal carbonyl coordination compounds of the iron group, viz., Fe, Ru, and Os carbonyl coordination compounds. Preferred are $Ru_3(CO)_{12}$ and $Os_3(CO)_{12}$, with $Ru_3(CO)_{12}$ being most preferred.

A catalytic amount of heated iron group carbonyl coordination compounds is required for the practice of this invention. Typically, the catalyst precursor is present at a minimum precursor:reactants weight ratio of about 1:1000 and preferably of about 1:700. These ratios are typical with the actual ratios determined by the specific catalysts and reactants used as well as practical considerations such as convenience and economy.

It is to be noted that the process of the invention may be advantageously carried out in batch, semi-batch or continuous reactors.

The temperature at which the reaction is carried out may vary from below to above 80° C. Too low of a temperature reduces the rate of reaction while too high of a temperature is not cost effective. The optimal temperature for a particular system of reactants and iron group compound may readily be determined without undue experimentation.

The reaction may also proceed under elevated or depressed as well as atmospheric pressures. However, it is to be noted that the reaction should not be carried out in an open vessel since the reaction mixture will generally have been degassed to remove dissolved oxygen which poisons the catalyst. In some cases excess carbon monoxide may also act to deactivate the catalyst and should be avoided. Degassing may be accomplished in various ways known to those skilled in the art. Two common methods are purging with nitrogen or subjecting the reaction vessel and its contents to repetitive freeze-pump-thaw cycles. Utilizing either method will allow the reaction to be carried out in an inert environment thereby preserving the catalyst and avoiding unwanted side reactions.

Reaction times from about 1 to about 20 hours are expected. Reaction time will generally be based upon practical considerations such as convenience, economy, catalyst choice as well as the particular reactants used.

Normally, substantially equivalent amounts of the organosilicon hydride are reacted with the carbonyl compound. However, the amounts of both reactants can be altered depending upon the degree of hydrosilylation desired.

The process of the invention can produce high yields of silyl ether products. However, care should be used to avoid the presence of water in the reaction as $H_2O$ competes with carbonyl compounds via side reactions with the organosilicon hydride reactants. For example,

The silyl ethers produced by the process of this invention have well-known utilities including use in industry in water-proofing agents, silicon lacquers, polymer transparency improving agents, siloxane polymer plasticizers and in the preparation of silicon resins. Moreover, silyl ethers are thermally stable and easily analyzed by conventional analytical techniques. Therefore, this invention may be employed to protect or analyze compounds containing an active hydrogen atom by the intermediate formation of organosilyl protected compounds.

Following are examples given to illustrate the process of the invention, but these examples should not be taken as limiting the scope.

Unless otherwise specified, the following reactions were all conducted utilizing as the reaction vessel, a Pyrex® tube equipped with a high vacuum stopcock and Teflon® plug. The carbonyl compounds and organosilicon hydrides were all distilled and kept dry over molecular sieve absorbents.

EXAMPLE 1

Catalytic Hydrosilylation of Acetone in Absence of Light

A reaction vessel was charged with 0.26 grams (0.33 ml, 0.0045 mole) acetone, 0.48 grams (0.66 ml, 0.0041 mole) of triethyl silicon hydride and ($3 \times 10^{-6}$ mole) of an iron group catalyst. An oil immersion bath was used to heat the reaction vessels. The reaction mixture was thoroughly degassed by four freeze-pump-thaw cycles. After degassing, the reaction mixture was heated for 20 hours at 80° C. and the contents were analyzed by standard vapor phase chromatographic techniques. The results are shown in Table I. All percentages in the tables are weight percent unless otherwise noted. Weight percentage is based upon starting amounts of triethyl silicon hydride.

TABLE I

| | Catalytic Hydrosilylation of Acetone in the Absence of Light | | | |
|---|---|---|---|---|
| # | Catalyst Precursor | Temp. °C. | Time (hr) | % $HSiEt_3$ Conversion |
| 1 | $Fe_3(CO)_{12}$ | 80 | 20 | 34 |
| 2 | $Ru_3(CO)_{12}$ | 80 | 20 | 100 |
| 3 | $Os_3(CO)_{12}$ | 80 | 20 | 76 |

Table I shows good activities for both the iron and osmium catalysts with exceptional activity noted in the reaction utilizing a ruthenium carbonyl compound.

EXAMPLE 2

Comparative Example

Example 1 was repeated under similar conditions but using transition metal carbonyl coordination compounds, not of the present invention, as catalysts. The results are shown in Table II.

TABLE II

| | Catalytic Hydrosilylation of Acetone in the Absence of Light | | | |
|---|---|---|---|---|
| # | Catalyst Precursor | Temp. °C. | Time (hr) | % $HSiEt_3$ Conversion |
| 1 | $Ir_4(CO)_{12}$ | 80 | 20 | 6 |
| 2 | $Re_2(CO)_{10}$ | 80 | 20 | 10 |
| 3 | $Co_4(CO)_{12}$ | 80 | 20 | 3 |

It may be seen from the results given in Table II that not all transition metal carbonyl coordination compounds have the same degree of catalytic activity. These conversions represent the poor results that are obtained in the absence of the transition carbonyl coordination compounds of the present invention.

EXAMPLE 3

Comparative Example

Examples 1 and 2 were both repeated under similar conditions but now at about 29° C. The results are given in Table III.

TABLE III

| | Catalytic Hydrosilylation of Acetone in the Absence of Light | | | |
|---|---|---|---|---|
| # | Catalyst Precursor | Temp. °C. | Time (hr) | % $HSiEt_3$ Conversion |
| 1 | $Ir_4(CO)_{12}$ | 29 | 20 | <1 |
| 2 | $Re_2(CO)_{10}$ | 29 | 20 | <1 |
| 3 | $Ru_3(CO)_{12}$ | 29 | 20 | <1 |
| 4 | $Os_3(CO)_{12}$ | 29 | 20 | <1 |
| 5 | $Co_4(CO)_{12}$ | 29 | 20 | <1 |
| 6 | $Fe_3(CO)_{12}$ | 29 | 20 | <1 |

It may be seen from Table III that conversion of triethyl silicon hydride, if conversion occurs at all, is less than one percent for both catalysts of the present invention and control catalysts. Since silyl ethers are not formed in appreciable amounts, this example represents a set of conditions not of the present invention.

As mentioned before, the above examples serve only to illustrate the invention and its advantages, and the examples of the invention should not be interpreted as limiting since further modifications of the disclosed invention will be apparent to those skilled in the art. All such modifications are deemed to be within the scope of the invention as defined by the following claims.

What is claimed is:

1. A process comprising contacting a carbonyl compound with an organosilicon hydride under reaction conditions to form a silyl ether in the presence of a catalytic amount of at least one iron group transition metal carbonyl coordination compound and elevated temperature.

2. A process as defined in claim 1 wherein said temperature is 35° C. or higher.

3. A process as defined in claim 2 wherein said temperature is in a range from about 60° C. to about 110° C.

4. A process as defined in claim 2 or 3 wherein said compound is $Ru_3(CO)_{12}$.

5. A process as defined in claim 2 or 3 wherein said compound is $Fe_3(CO)_{12}$.

6. A process as defined in claim 2 or 3 wherein said compound is $Os_3(CO)_{12}$.

7. A process comprising reacting a carbonyl compound with an organosilicon hydride under reaction conditions to form a silyl ether in the presence of a thermally activated species of triruthenium dodecacarbonyl, triosmium dodecacarbonyl, triiron dodecacarbonyl or mixtures thereof.

8. A process as defined in claim 4 wherein said carbonyl compound is a ketone.

9. A process as defined in claim 8 wherein said organosilicon hydride is triethyl silicon hydride.

10. A process as defined in claim 5 wherein said carbonyl compound is a ketone.

11. A process as defined in claim 10 wherein said organosilicon hydride compound is triethyl silicon hydride.

* * * * *